United States Patent [19]

Large et al.

[11] 4,083,970
[45] Apr. 11, 1978

[54] ACTIVATED INSECTICIDE COMPOSITION EMPLOYING A CERTAIN PHOSPHORODITHIOATE AND AN ACTIVATOR

[75] Inventors: George B. Large, Orinda, Calif.; Leland S. Pitt, Greenville, Miss.

[73] Assignee: Stauffer Chemical Company, Westport, Conn.

[21] Appl. No.: 770,532

[22] Filed: Feb. 22, 1977

Related U.S. Application Data

[63] Continuation-in-part of Ser. No. 753,233, Dec. 10, 1976, abandoned, which is a continuation of Ser. No. 619,999, Oct. 6, 1975, abandoned, which is a continuation-in-part of Ser. No. 537,145, Dec. 30, 1974, Pat. No. 3,956,486.

[51] Int. Cl.$^2$ ............................................. A01N 9/36
[52] U.S. Cl. ................................. 424/200; 424/220
[58] Field of Search ................................ 424/200, 220

[56] References Cited

U.S. PATENT DOCUMENTS

| 3,720,735 | 3/1973 | Martin et al. | 424/220 |
| 3,892,854 | 7/1975 | Drabek | 424/200 |

Primary Examiner—V. D. Turner
Attorney, Agent, or Firm—M. Henry Heines; Daniel C. Block

[57] ABSTRACT

A composition of matter is described herein which is useful as an activated insecticide. The composition comprises a mixture of an insecticide and an activator, said activator defined by the formula:

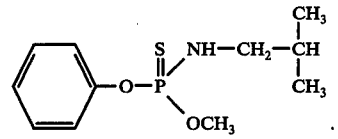

2 Claims, No Drawings

ACTIVATED INSECTICIDE COMPOSITION EMPLOYING A CERTAIN PHOSPHORODITHIOATE AND AN ACTIVATOR

CROSS REFERENCE TO RELATED APPLICATIONS

This application is a continuation-in-part of copending application Ser. No. 753,233, filed Dec. 10, 1976, now abandoned which is a continuation of application Ser. No. 619,999, filed Oct. 6, 1975, now abandoned, which in turn is a continuation-in-part of application Ser. No. 537,145, filed Dec. 30, 1974, now U.S. Pat. No. 3,956,486.

BACKGROUND OF THE INVENTION

Among the many insecticidal compounds, the benzotriazine thiophosphates have reached a relatively high degree of commercial success. These compounds are toxic to a large number of insect pests at different concentrations varying with the degree of susceptibility of the insects mentioned. Some of these compounds are described in U.S. Pat. No. 2,758,115, specifically O,O-dimethyl S[4-oxo-1,2,3-benzotriazin-3(4H)-ylmethyl]-phosphorodithioate.

The endeavor to extend the usefulness of the thiophosphates by increasing their effectiveness and lowering their cost has led to extensive studies on another class of biologically active chemicals, customarily referred to as activators. Among the many activators employed, the alkyl oxides, specifically, piperonyl butoxide, have been widely used. These compounds are described in U.S. Pat. Nos. 2,485,681 and 2,550,737.

DETAILED DESCRIPTION OF THE INVENTION

It has been discovered that the activity of insecticidally active thiophosphate compounds can be increased by using an activator having the formula

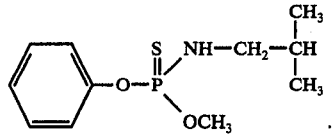

The activator compound is manufactured by reacting isobutylamine with an O-methyl-O-phenylthiophosphoryl halide. The end product is isolated, purified, and admixed with the insecticidal compound. The amount of activator admixed therewith can range from about 1:0.1 to about 1:10 parts insecticidal compound to activator compound. The insecticide-activator mixture is applied to the habitat of the insect in a conventional manner.

In order to illustrate the merits of the present invention, the following example is provided:

EXAMPLE

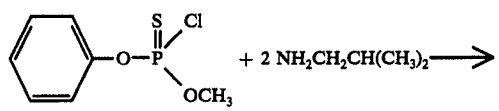

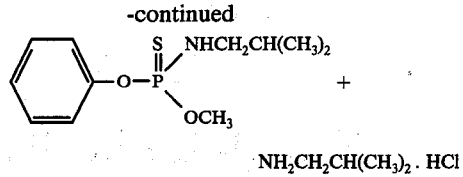

$NH_2CH_2CH(CH_3)_2 \cdot HCl$

A solution was formed containing 5.55 parts by weight of O-methyl-O-phenylphosphorothiochloridate in benzene. As the solution was stirred, 4.38 parts by weight of isobutylamine were added. A temperature rise was detected and the reaction mixture was stirred for an additional thirty minutes after addition was complete. The reaction mixture was then washed successively with 1N HCl solution and water. The organic phase was dried over anhydrous $MgSO_4$. The volatiles were then removed from the mixture under reduced pressure to yield 6.2 parts by weight of product, or 96% yield. The product had a refractive index of $n_D^{30} = 1.4972$, and its structure was confirmed by infrared and nuclear magnetic resonance spectra as that of O-methyl-O-phenylisobutylphosphoramidothioate.

The above compound and the insecticide O,O-dimethyl S[4-oxo-1,2,3-benzotriazin-3(4H)-ylmethyl]-phosphorothioate, both singly and in combination, were tested for insecticidal activity by the following procedures.

INSECTICIDAL EVALUATION

A. Housefly [*Musca domestica* (L.)]

Test compounds are diluted in acetone and aliquots are pipetted onto the bottom of 55 × 15 mm aluminum dishes. To insure even spreading of the chemical on the bottom of the dishes, 1 ml of acetone containing 0.02% peanut oil is also added to each dish. After all solvents have evaporated the dishes are placed in circular cardboard cages containing 25 3-day-old female houseflies. The cages are covered on the bottom with cellophane and the top with tulle netting, and each contains a sugar-water saturated cotton plug for maintenance of the flies. Mortality is recorded after 48 hours. One part activator is combined with one part toxicant in all stock solutions. Test levels range from 100 μg toxicant + 100 μg of activator down to that at which approximately 50% mortality occurs. All $LD_{50}$ values are expressed as μg of toxicant/dish.

B. Cabbage Looper [*Trichoplusia ni*]

Test solutions are prepared by dissolving equal aliquots of the toxicant and activator in a 50-50 acetone-water solution. Cotyledons of squash [*Curcurbita pepo*] are immersed in the test solutions for 1 to 2 seconds and placed on a wire screen to dry. The dried leaves are placed on a moistened piece of filter paper in a Petri dish and infested with 5 third-instar larvae. Test concentrations for both toxicant and activator range from 0.1% down to that at which 50% mortality occurs. Mortality of the larvae is recorded after 48 hours and the $LD_{50}$ values are expressed as percent toxicant in the acetone-water solutions.

C. Tobacco Budworm [*Heliothis virescens* (F.)]

The procedure is the same as that used for the Cabbage Looper, except that leaves of Romaine lettuce [*Latuca sativa*] are utilized as the host plant rather than squash.

D. German Cockroach [*Blatella germanica* (Linne)]

Equal aliquots of toxicant and activator are diluted in a 50–50 acetone-water solution. Two cc of the solutions are sprayed through a DeVilbiss type EGA hand spray gun into circular cardboard cages containing 10 1-month-old German Cockroach nymphs. The test cages are covered on the bottom with cellophane and the top with tulle netting. Percent mortality is recorded 2 days later. Test concentrations range from 0.1% down to that at which 50% mortality occurs. All $LD_{50}$ values are expressed as percent toxicant.

ACTIVATING FACTOR

The activating factor (A.F.) is computed by the following formula:

$$A.F. = \frac{LD_{50} \text{ of Toxicant}}{\text{Experimental } LD_{50} \text{ of Combination}} \cdot \frac{1}{(XY + 1)},$$

where  X = the weight ratio of activator to toxicant, and
Y = the ratio of the $LD_{50}$ of the toxicant to the $LD_{50}$ of the activator.

The experimental $LD_{50}$ of the combination is in terms of the toxicant only.

The activating factor is therefore the expected $LD_{50}$ of the combination divided by the experimental $LD_{50}$. It is noted that when the observed response is greater than the expected, the activating factor is greater than one. The results of these tests are set forth in the following table.

TABLE

Contact Activity: Approximate $LD_{50}$ Values

| Insect | Activator Alone | Insecticide Alone | 1:1 Comb. | Activating Factor |
|---|---|---|---|---|
| Housefly (μg/25 flies) | 250. | 3.6 | 2.5 | 1.4 |
| Cabbage Looper (%) | .08 | .007 | .006 | 1.1 |
| Tobacco Budworm (%) | .2 | .025 | .008 | 2.8 |
| German Cockroach (%) | .83 | .008 | .002 | 4.0 |

Activator: O-methyl-O-phenylisobutylphosphioramidothioate
Insecticide: O,O-dimethyl S[4-oxo-1,2,3-benzotriazine-3(4H)- ylmethyl]-phosphorothioate.

The composition of this invention is generally embodied in a formulation suitable for convenient application. In general, such a formulation will contain inert or occasionally active ingredients or diluent carriers in addition to the active compound. Examples of such ingredients or carriers are organic solvents, such as sesame oil, xylene range solvents, and heavy petroleum; water; emulsifying agents; surface active agents; talc; pyrophyllite; diatomite; gypsum; clays; and propellants, such as dichlorodifluoromethane.

The active composition can be combined with dust carriers for application as dusts, with granular carriers for application by fertilizer spreaders or ground or airplane seeders, with wettable powders or flowable carriers for application as water suspensions, and with solvents and surface active materials for application as sprays, aerosols, or emulsions. The compositions can be applied to any habitat of the pests, for example dwellings, clothing, plant and insect surfaces, soil, etc. If desired, however, the active composition can be applied directly to feedstuffs, seeds, etc., upon which the pests feed. When applied in such a manner, it will be advantageous to use a composition which is not volatile.

The amount of active composition of formulation which is considered to be insecticidally effective is that amount which, when applied to the pest habitat, will kill or substantially injure a significant portion residing thereon. The amount of activator which is considered to be effective is that amount which, when in combination with the insecticidally active thiophosphate compound, results in a composition of matter whose insecticidal activity is greater than that of either of its components when the latter are applied individually.

In connection with the activity of the presently disclosed pesticidal composition, it should be fully understood that it is not necessary that it be active as such. The purposes of this invention will be fully served if the composition is rendered active by external influences, such as light, or by some physiological action which occurs when the preparation is ingested or penetrates into the body of the pest.

The precise manner in which the pesticidal composition of this invention is used in any particular instance will be readily apparent to a person skilled in the art. Generally, the active pesticidal composition will be embodied in the form of a liquid composition; for example, an emulsion, suspension, or aerosol spray. While the concentration of the active pesticidal composition in the present formulation can vary within rather wide limits, ordinarily, the pesticide composition will comprise not more than about 50.0% by weight of the formulation.

What is claimed is:

1. An insecticidally active composition comprising an insecticidally effective amount of an insecticide defined as O,O-dimethyl S[4-oxo-1,2,3-benzotriazin-3(4H)-ylmethyl]-phosphorodithioate and an effective amount of an activator having the formula

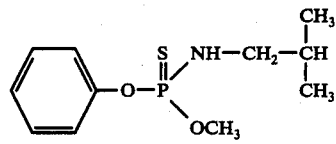

in a weight ratio of insecticide to activator of about 1:0.1 to about 1:10.

2. The method of controlling insects comprising applying to the habitat thereof an insecticidally effective amount of an insecticidally active composition comprising an insecticidally effective amount of an insecticide defined as O,O-dimethyl S[4-oxo-1,2,3-benzotriazin-3(4H)-ylmethyl]-phosphorodithioate and an effective amount of an activator having the formula

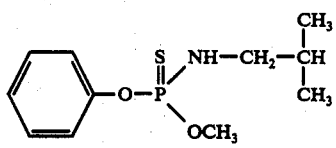

in a weight ratio of insecticide to activator of about 1:0.1 to about 1:10.

* * * * *